(12) United States Patent
Deller et al.

(10) Patent No.: US 8,229,187 B2
(45) Date of Patent: Jul. 24, 2012

(54) RESPIRATORY MOTION EXTRACTION FROM TOMOGRAPHIC PROJECTION AND IMAGE DATA

(75) Inventors: Timothy W Deller, Waukesha, WI (US); Kelly L Piacsek, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 1052 days.

(21) Appl. No.: 11/734,245

(22) Filed: Apr. 11, 2007

(65) Prior Publication Data

US 2008/0253636 A1 Oct. 16, 2008

(51) Int. Cl.
*G06K 9/00* (2006.01)

(52) U.S. Cl. ...................................... 382/128

(58) Field of Classification Search ........ 382/128–134; 128/920–930; 250/455–465; 356/39–49; 600/407–414, 424–426
See application file for complete search history.

(56) References Cited

U.S. PATENT DOCUMENTS

| | | | | |
|---|---|---|---|---|
| 6,421,552 | B1* | 7/2002 | Hsieh | 600/425 |
| 2004/0125908 | A1* | 7/2004 | Cesmeli et al. | 378/4 |
| 2004/0258286 | A1 | 12/2004 | Salla et al. | |

OTHER PUBLICATIONS

Lu W et al: "tomography motion detection and correction directly in sinogram space" Physics in Medicine and Biology, Taylor Ano Francis Ltd. London, GB, nr 47, Apr. 5, 2002, bladzijden 1267-1284, XP002438716 ISSN: 0031-9155.

Kachelriess Marc et al: "Kymogram detection and kymogram-correlated image reconstruction from subsecond spiral computed tomography scans of the heart" Medical Physics, AIP, Melville, NY, US, deel 29, nr . 7, Jul. 1, 2002, bladzijden 1489-1503, XP012011846 ISSN: 0094-2405.

Saeed Sarkar et al: "A Linogram/Sinogram Cross-Correlation Method for Motion Correction in Planar and SPECT Imaging" IEEE Transactions on Nuclear Science,-IEEE Service Center, New York, NY, US, deel 54, nr. 1, Feb. 1, 2007, bladzijden 71-79, XP011163940 ISSN: 0018-9499.

Eisner R L et al: "Use of Cross-Correlation Function to Detect Patient Motion During SPECT Imaging" Journal of Nuclear Medicine, Society of Nuclear Medicine, Reston, VA, US, deel 28, nr. 1, Jan. 1, 1987, bladzijden 97-101, XP002033864 ISSN: 0161-5505.

Passalaqua A M et al: "Patient motion correction of SPECT images: dual scan approach" Nuclear Science Symposium and Medical Imaging Conference, 1994 , 1994 IEEE Conference Record Norfolk, VA, USA Oct. 30-Nov. 5, 1994, New York, NY, USA,IEEE, US. deel 3, Oct. 30, 1994, bladzijden 1270-1274, XP010150377 ISBN: 978-0/7803-2544-9, bladzijden 1270 en 1272, derde alinea.

(Continued)

*Primary Examiner* — Atiba O Fitzpatrick
(74) *Attorney, Agent, or Firm* — Rick Washer, Esq.; Michael G. Smith, Esq.

(57) ABSTRACT

The present technique provides a novel method and apparatus for determining the motion of an internal tissue or organ undergoing dynamic movement such as a respiratory cycle. Particularly, the technique provides for a method and system for processing projection data to determine the motion rather than relying on additional data acquired from an external sensor. The motion is extracted from projection data by tracking the change over time in projections from the same projection angle and/or conjugate projection angle pairs. The extraction is possible because multiple gantry rotations occur in the time period of a single respiratory period. The motion information may in turn be used to facilitate data acquisition or image reconstruction, such as by gating techniques, to reduce or eliminate motion related artifacts.

20 Claims, 7 Drawing Sheets

OTHER PUBLICATIONS

Jiang Hsieh ED—Hsieh J: "Computed Tomography passage" Computed Tomography : Principles, Design, Artifacts. and Recent Advances. Belligham, WA : SPIE'; US, Jan. 1, 2003, bladzijden 212-221, XP002505684 ISBN: 978-0-8194-4425-7.

Feng et al: "Estimation of the Rigid-Body Motion From Three-Dimensional Images Using a Generalized Center-of-Mass Points Auuroach" Relevante Literatuur IEEE Transactions on Nuclear Science, IEEE Service Center, New York, NY, US, deel 53, nr. 5, Oct. 1, 2006. bladzijden 2712-2718, XP011149543 ISSN: 0018-9499.

Mageras G. et al., Initial clinical evaluation of a respiratory gating radiotherapy system, Engineering in Medicine and Biology Society, 2000, Proceedings of the 22nd Annual International Conference of the IEEE (2000), vol. 3, pp. 2124-2127.

* cited by examiner

RESPIRATORY MOTION EXTRACTION FROM TOMOGRAPHIC PROJECTION AND IMAGE DATA

FIELD OF THE INVENTION

This invention relates generally to imaging systems and methods, and more particularly to systems and methods for extracting the motion of an object being imaged.

BACKGROUND OF THE INVENTION

Many medical imaging applications require knowledge of patient respiratory activity. Applications such as radiation therapy planning and pediatric imaging without breath hold can benefit from extraction of respiratory motion during the image acquisition process.

Current methodology utilizes an external sensor to obtain this respiratory activity or respiratory waveform since the breathing cycle exhibits different phases. An example of such a system uses the Varian Real-Time Position Management (RPM) Respiratory Gating System. See, Mageras G. et al., *Initial clinical evaluation of a respiratory gating radiotherapy system*, Engineering in Medicine and Biology Society, 2000, Proceedings of the 22nd Annual International Conference of the IEEE (2000), Volume 3, Pages 2124-2127. The RPM tool places a small reflective marker on the chest wall of the patient, and a video monitor tracks its position. Video analysis and signal processing steps produce the respiratory waveform based on the movement of the sensor throughout the respiratory cycle. In addition to complicating the patient setup and radiotherapy planning workflow, these respiratory monitoring devices can be expensive.

In four dimensional Computed Tomography (4DCT) respiratory gating utilizes a small reflective marker placed on the patient's chest or abdomen that can be detected by an infrared camera placed at the foot of the patient table. Respiratory gating allows therapists to track the patient's respiratory cycle both at the time of the CT scan for imaging and at the time of treatment. As the patient breathes, the marker is vertically displaced according to the patient's respiratory cycle and the infrared camera records the position of the marker. This information is then used to determine the patient respiratory phase at the time of Computed Tomography (CT) image acquisition. CT images are generated at multiple locations along the patient's chest and abdomen. The CT images are then retrospectively sorted into phases according to the information recorded by the infrared camera. The result of reconciling the images to the infrared camera respiratory waveform is a four dimensional (4D) image set. This 4D image set consists of a 3D volumetric image data set generated for each of multiple respiratory phases, image set of the lungs and surrounding area throughout the respiratory cycle. This is particularly useful for radiation therapy, as it is clinically relevant to understand the motion of lung and abdominal tumors throughout the respiratory cycle in order to properly plan radiation treatment. As radiation therapy technology emerges, high quality 4D reconstructions and easily implemented respiratory gating capability become increasingly important for precise tumor tracking and minimization of patient preparation and planning time.

For the reasons stated above, and for other reasons stated below which will become apparent to those skilled in the art upon reading and understanding the present specification, there is a need in the art for extracting motion from projection data that is directly related to actual respiratory activity.

BRIEF DESCRIPTION OF THE INVENTION

The above-mentioned shortcomings, disadvantages and problems are addressed herein, which will be understood by reading and studying the following specification.

The present technique provides a novel method and apparatus for determining the motion of an internal tissue or organ undergoing dynamic movement such as a respiratory cycle. Particularly, the technique provides for a method and system for processing acquired projection data to determine the motion. The motion information may in turn be used to facilitate data acquisition or image reconstruction, such as by gating techniques, to reduce or eliminate motion related artifacts.

In one aspect, a method is provided for extracting motion from an acquired set of projection data. The acquired set of projection data is analyzed to extract timing information by tracking the changes over time of the center of mass of the tissue being monitored. Phase calculations are then performed on the timing information from one or more projection angle. The extracted motion waveform is used to synchronize CT images produced by a CT detector system with the motion of the tissue.

In another aspect, a method is provided for extracting motion from an acquired set of projection data. The acquired set of projection data is analyzed to extract timing information by tracking the changes over time of the center of mass of the tissue being monitored. Peak, phase, rate of change calculations are then performed on the timing information from one or more projection angle.

In yet another aspect, an apparatus is provided for extracting motion from projection data acquired a CT detector system. A processor, storage device, and software means are combined to acquire projection data to track the changes over time of the center of mass of a tissue being monitored. The processor as directed by the software means then samples the data at one or more projection angle to produce a motion waveform expressing the respiratory cycle.

In still another aspect, a computer-accessible medium having executable instructions for extracting motion from a rotating gantry in a CT detector system, the executable instructions capable of directing a processor to acquire projection data and to process the acquired projection data to produce a motion waveform expressing the respiratory cycle.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
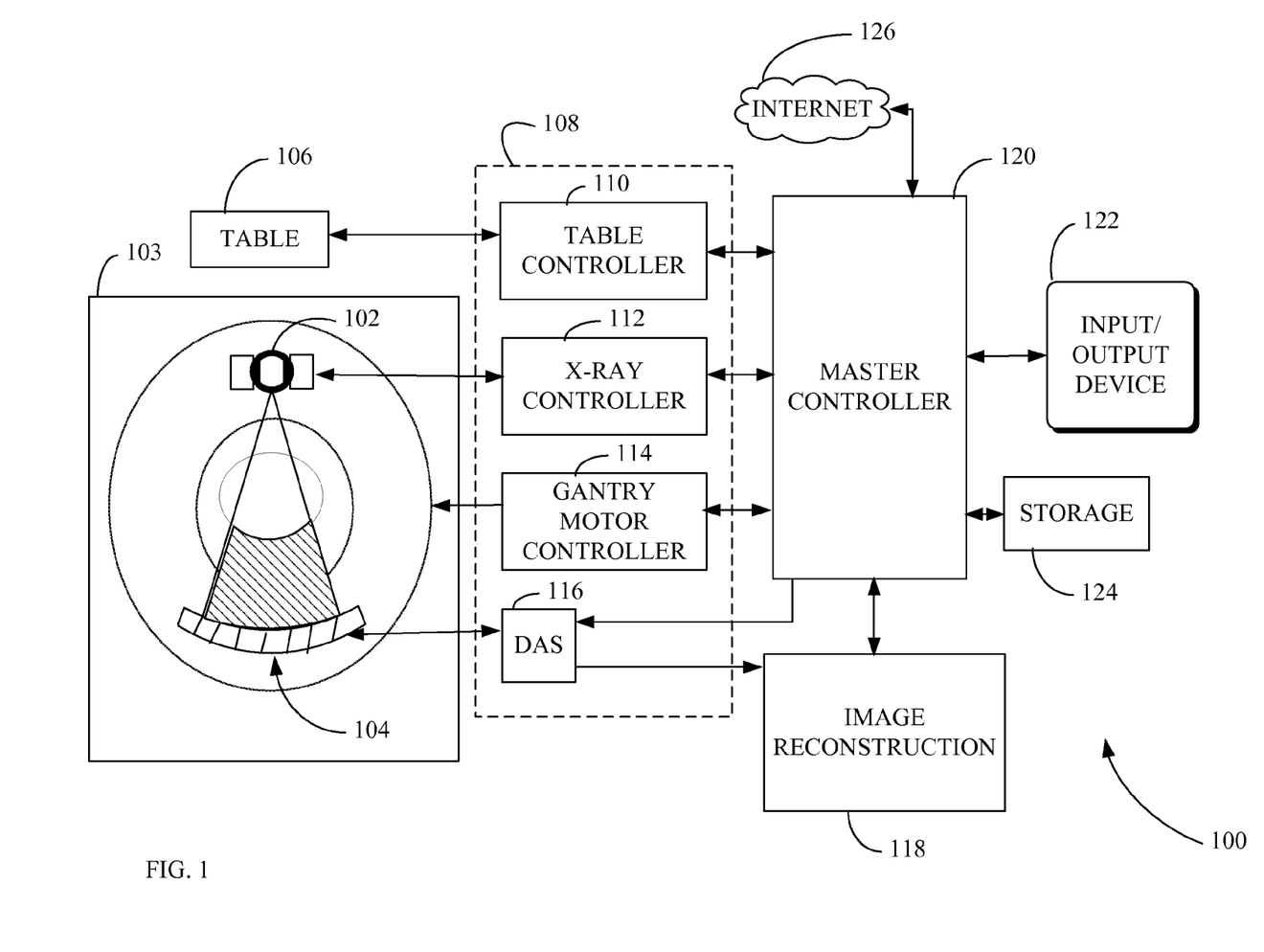
FIG. 1 is a diagram illustrating a system-level overview of an embodiment for acquiring projection data.

FIG. 1 is a block diagram of an overview of a system for acquiring medical images. CT imaging system 100 solves the need in the art for managing advanced medical diagnostic imaging applications executing on a network or a computer. CT imaging system 100 includes a gantry 103, table 106, controllers 108, master controller, and image reconstruction device 118. It should be noted that other data acquisition systems are envisioned including a magnetic resonance (MRI) imaging system, a positron emission tomography (PET) system, a single photon emission computed tomography (SPECT) system, an ultrasound system, or an X-ray system. The data acquisition system obtains data including, but not limited to image data, functional image data, and temporal image data. Further examples of data include voxel data including volume information for a three dimensional region of interest (ROI), pixel data including area information for a two dimensional region of interest, and spatio-temporal data. Spatio-temporal data includes area or volume information over a selected, predetermined time period.

CT imaging system 100 includes a gantry 103 having an X-ray source 102, a radiation detector array 104, a patient support structure and a patient cavity, wherein the x-ray source 102 and the radiation detector array 104 are diametrically disposed so as to be separated by the patient cavity. In an exemplary embodiment, a patient (not shown) is disposed upon the patient support structure, which is then disposed within the patient cavity. The x-ray source 102 projects an X-ray beam toward the radiation detector array 104 so as to pass through the patient. In an exemplary embodiment, the X-ray beam is collimated by a collimate (not shown) so as to lie within an X-Y plane of a Cartesian coordinate system known to those in the art as the imaging plane. After becoming attenuated by the patient passing through, the attenuated X-ray beam is received by the radiation detector array 104. In the preferred embodiment, the radiation detector array 104 includes a plurality of detector elements wherein each of said detector elements receives an attenuated X-ray beam and produces an electrical signal responsive to the intensity of the attenuated x-ray beam.

In addition, the X-ray source 102 and the radiation detector array 104 can rotate relative to the gantry 103 and the patient support structure, so as to allow the X-ray source 102 and the radiation detector array 104 to rotate around the patient support structure when the patient support structure is disposed within the patient cavity. X-ray projection data is obtained by rotating the X-ray source 102 and the radiation detector array 104 around the patient during a scan. The X-ray source 102 and the radiation detector array 104 communicate with a control mechanism 108 associated with the CT imaging system 100. The control mechanism 108 controls the rotation and operation of the x-ray source 102 and the radiation detector array 104.

The table controller 110, X-ray controller, gantry motor controller, DAS 116, image reconstruction 118, and master controller 120 have the same hardware and capabilities limited only by the programming in each respective device. For the purpose of the description, all controllers are presumed to have the same hardware so a discussion to one applies to all. The master controller 120 provides computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

The master controller 120 includes a processor, commercially available from Intel, Motorola, Cyrix and others. Master controller 120 also includes random-access memory (RAM), read-only memory (ROM), and one or more mass storage devices 124, and a system bus that operatively couples various system components to the processing unit of master controller 120. The memory and mass storage devices are types of computer-accessible media. Mass storage devices are more specifically types of nonvolatile computer-accessible media and can include one or more hard disk drives, floppy disk drives, optical disk drives, and tape cartridge drives. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory. The processor in the master controller executes computer programs stored on the computer-accessible media.

Master controller 120 can be communicatively connected to the Internet 126 via a communication device. Internet 126 connectivity is well known in the art. In one embodiment, a communication device is a modem that responds to communication drivers to connect to the Internet via what is known in the art as a "dial-up connection." In another embodiment, a communication device is an Ethernet® or similar hardware network card connected to a local-area network (LAN) that itself is connected to the Internet via what is known in the art as a "direct connection" (e.g., T1 line, etc.).

A user enters commands and information into the master controller 120 through input device 122 such as a keyboard or a pointing device. The keyboard permits entry of textual information into master controller 120, as known within the art, and embodiments are not limited to any particular type of keyboard. Pointing device permits the control of the screen pointer provided by a graphical user interface (GUI) of operating systems such as versions of Microsoft Windows®. Embodiments are not limited to any particular pointing device. Such pointing devices include mice, touch pads, trackballs, remote controls and point sticks. Other input devices (not shown) can include a microphone, joystick, game pad, satellite dish, scanner, or the like. For the purpose of this description, a keyboard and a pointing device are referred to as a user interface (UI). The UI allows the user to interact with any of components in the imaging system, algorithm within any of before mentioned devices, or structure or firmware in any of the devices. The output device is a display device. Display device is connected to a system bus. Display device permits the display of information, including images, text, video and other information, for viewing by a user of the computer. Embodiments are not limited to any particular display device. Such display devices include cathode ray tube (CRT) displays (monitors), as well as flat panel displays such as liquid crystal displays (LCD's). In addition to a monitor, computers typically include other peripheral input/output devices such as printers (not shown). The controllers also include an operating system (not shown) that is stored on the computer-accessible media RAM, ROM, and mass storage device 124, and executed by the processor in the controller. Examples of operating systems include Microsoft Windows®, Apple MacOS®, Linux®, UNIX®. Examples are not limited to any particular operating system, however, and the construction and use of such operating systems are well known within the art.

Master controller 120 can be operated using at least one operating system to provide a graphical user interface (GUI) including a user-controllable pointer. Master controller can have at least one web browser application program executing within at least one operating system, to permit users of the controller to access intranet or Internet world-wide-web pages as addressed by Universal Resource Locator (URL) addresses. Examples of browser application programs include Netscape Navigator® and Microsoft Internet Explorer In an exemplary embodiment, the control mechanism 108 includes an X-ray controller 112 communicating with an X-ray source 102, a gantry motor controller 114, and a data acquisition system (DAS) 116 communicating with a radiation detector array 104. The X-ray controller 112 provides power and timing signals to the X-ray source 102, the gantry motor controller 114 controls the rotational speed and angular position of the x-ray source 102, and the radiation detector array 104 and the DAS 116 receive the electrical signal data produced by detector elements 104 and convert this data into digital signals for subsequent processing. In an exemplary embodiment, the CT imaging system 100 also includes an image reconstruction device 118, a data storage device 124 and a master controller 120, wherein the processing device 120 communicates with the image reconstruction device 118, the gantry motor controller 114, the x-ray controller 112, the data storage device 124, an input and an output device 122. The CT imaging system 100 can also include a table controller 110 in communication with the master controller 120 and the patient support structure, so as to control the position of the patient support structure relative to the patient cavity.

In accordance with the preferred embodiment, the patient is disposed on the patient support structure, which is then positioned by an operator via the master controller 120 so as to be disposed within the patient cavity. The gantry motor controller 114 is operated via master controller 120 so as to cause the X-ray source 4 and the radiation detector array 6 to rotate relative to the patient. The X-ray controller 112 is operated via the master controller 120 so as to cause the X-ray source 102 to emit and project a collimated X-ray beam toward the radiation detector array 104 and hence toward the patient. The X-ray beam passes through the patient so as to create an attenuated X-ray beam, which is received by the radiation detector array 104.

The detector elements 104 receive the attenuated X-ray beam, produce electrical signal data responsive to the intensity of the attenuated x-ray beam and communicate this electrical signal data to the DAS 116. The DAS 116 then converts this electrical signal data to digital signals and communicates both the digital signals and the electrical signal data to the image reconstruction device 118, which performs high-speed image reconstruction. This information is then communicated to the master controller 120, which stores the image in the data storage device 124 and displays the digital signal as an image via output device 122. The information communicated to the master controller 120 is referred to as ROI image data. In accordance with an exemplary embodiment, the output device 122 includes a display screen having a plurality of discrete pixel elements.

Figure 2:
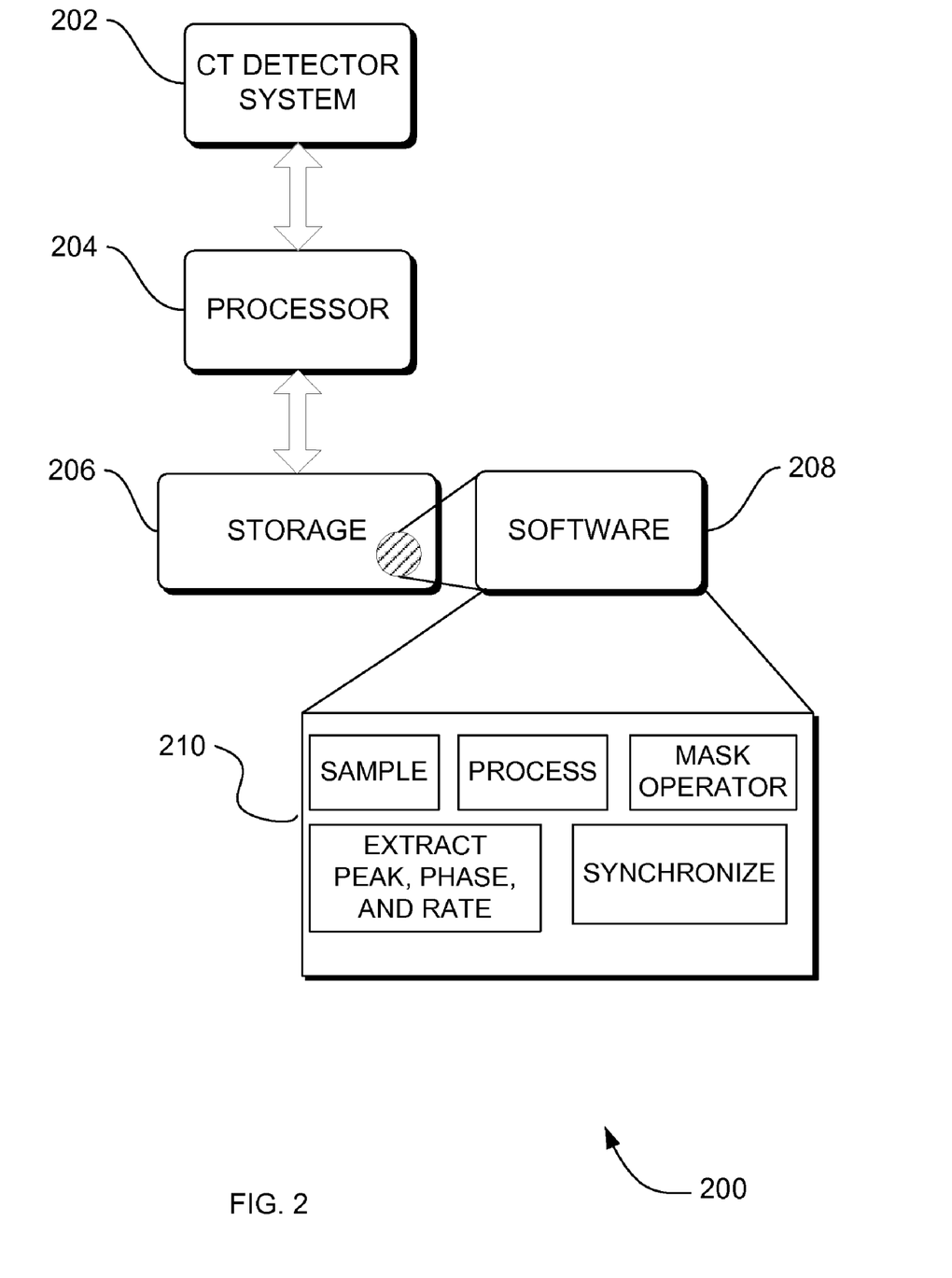
FIG. 2 is a block diagram of a hardware and operating environment in which different embodiments can be practiced for extracting motion from projection data.

FIG. 2 illustrates a system overview of a device 200 for extracting motion from projection data acquired with a CT detector system 100 in FIG. 1. The system comprises a CT detector system (202), processor 204, storage device 206, and software device 208 having objects 210 for performing analysis on projection data from the CT detector system 202. The software objects 210 perform sampling of projection data at a desired set of projection angles. Further, an object such as a mask operator can crop or truncate the projection data to remove unwanted regions in an image. Further, the software modules can track the change over time in projections from the same projection angle and/or conjugate projection angle pair to derive peak, phase, and rate for the respiratory cycle (respiratory waveform). The respiratory cycle can be used to synchronize image data with the quiescent period of the respiratory cycle, avoiding motion artifacts. This allows patients with difficulty controlling their breath to have data collected during free breathing and to free scan room from the need to accommodate sensing devices for tracking the respiratory cycle.

Figure 3:
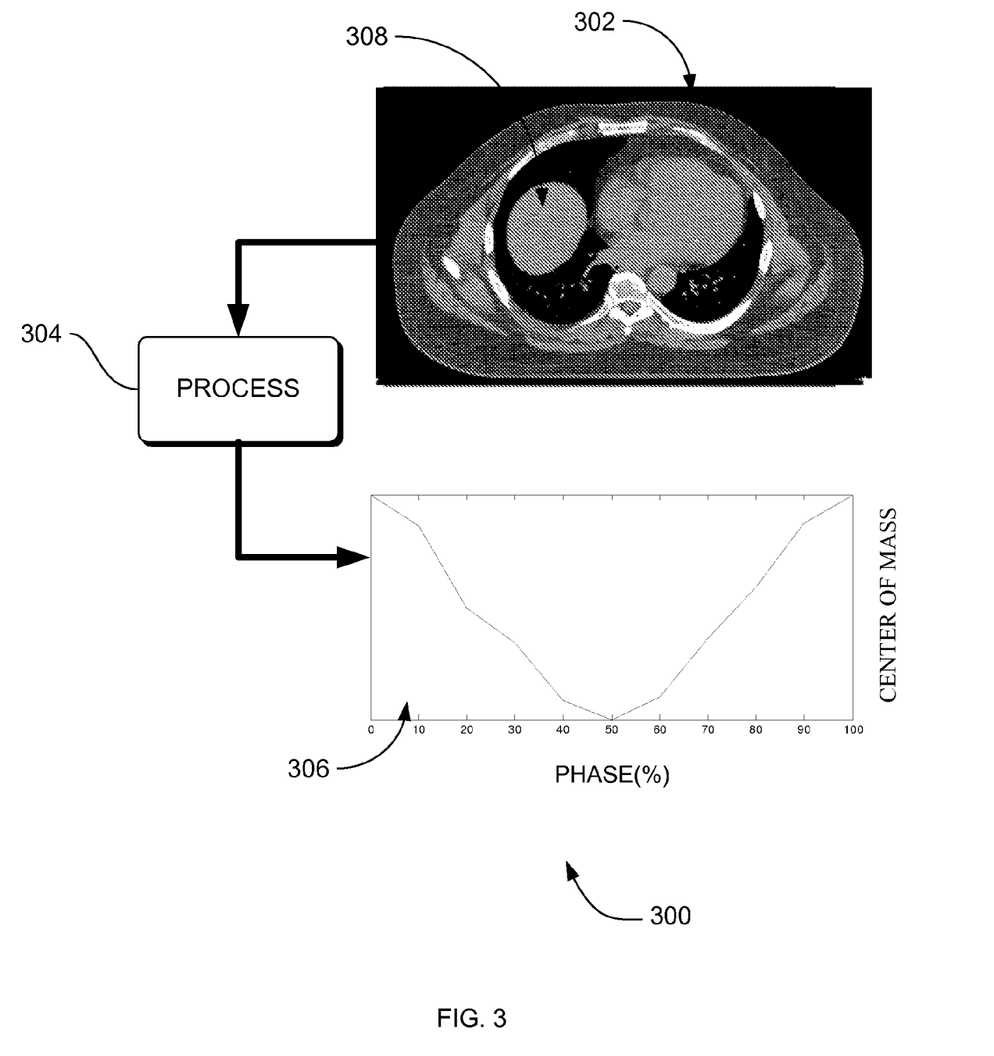
FIG. 3 is a system-level overview illustrating the relationship between center of mass and respiratory phase.

FIG. 3 illustrates the overall concept of extracting motion from projection data. As shown projection data is acquired, as depicted by action 502 of FIG. 5, such as by the helical operation of a multi-slice detector CT system or by operation of a volumetric CT system. Item 302 is an axial slice derived from the acquired projection data. The projection data is analyzed/processed 304 over the available respiratory cycles. In the case of a helical acquisition, the projection data may include both the measured projection data as well as interpolated projection data generated by a helical interpolation technique, as is well known to those skilled in the art. All or part of the projection data may be analyzed by applying a mask operator. In particular, subsequent analysis may be limited to a subset of the projection data if the subset corresponding to the region of interest can be identified and extracted. Analysis of the subset of projection data may provide a superior signal-to-noise ratio in the region of interest compared to analysis of the full set of projection data. The center of mass correlates with the respiratory cycle as shown in item 306. Since respiratory motion is relatively slow (10-20 breaths per minute) and the gantry mechanism rotates relatively quickly (less than or equal to 1 s per rotation) the respiratory cycle can be accurately captured with a CT detector system 100.

Figure 4:
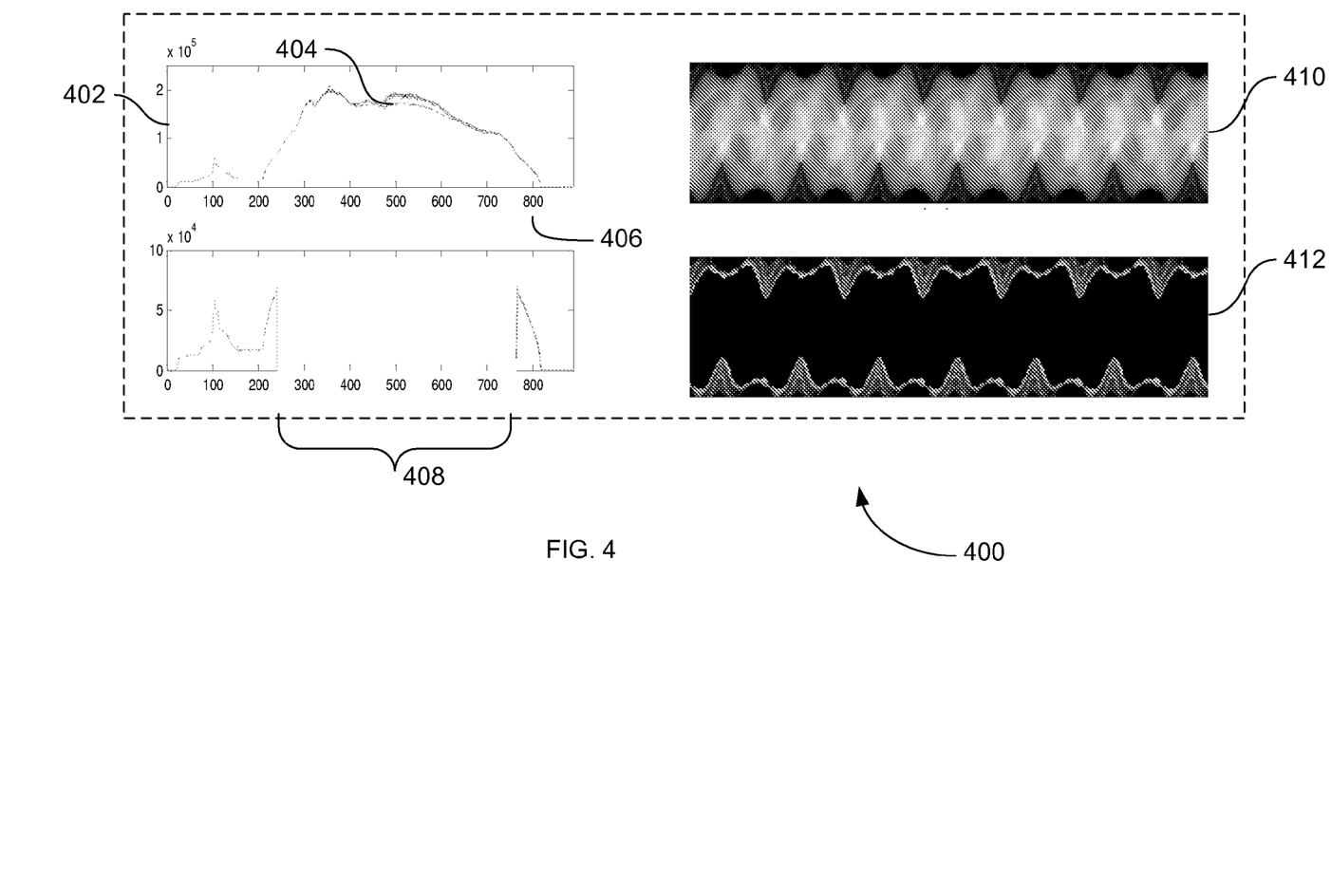
FIG. 4 is a representation of projection intensity, removing the center portion of the projection data, and projection data represented as a sinogram.

FIG. 4 shows projection data represented in Cartesian coordinate 402 and projection data represented as a sinogram 410. Rotation of the gantry assembly 114 around a subject results in X-ray data being acquired by detector elements (not shown) for a range of view angles, θ. A typical detector array 104 may comprise several hundred individual detector elements, such as 888 individual elements. The array 104 is positioned on the gantry at a predetermined distance (m) from the x-ray source 102. The circular path of source 102 has a radius that is proportional to the predetermined distance. Particular values of these parameters are not critical to the present invention and may be varied according to well-known principles of CT system design. One complete gantry rotation for the gantry 114 may comprise, for example, 984 view angles. Source 102 is thereby positioned to illuminate the subject successively from 984 different directions (θ) and the detector array 104 generates X-ray data at each view angle (θ), from which projection data for separate projection views are acquired. In the Cartesian projection data 402 the x-axis is CT detector channel 404 and y-axis is attenuation value 404. Each detector element (channel 404) produces a signal affected by the attenuation of the X-ray beams, and the data are processed to produce signals that represent the line integrals of the attenuation coefficients of the object along the X-ray paths. These signals are typically called projection data or just projections. The channel index α(=1, 2, . . . , α) is a sequential number given to the channels in each detector row.

There are occasions when the dynamics of certain organs can effect the determination of the respiratory cycle. FIG. 3 shows an example axial slice at peak inspiration. Due to the liver motion 308 in the z-direction, the slight change in the chest-wall height is difficult to detect by center-of-mass based approaches alone. The x-dimension and y-dimension center-of-mass of the slice is dominated by the liver motion 308 in the z-dimension. An approach is presented in FIG. 4 that focuses the center-of-mass analysis on the outside portion of the region of interest where the respiratory signal is most evident. The projections with the center portion removed. The interference from the liver (FIG. 3) is eliminated. This is accomplished by masking the inner portion of each projection. This mask is calculated for each fixed projection angle as shown in FIG. 4. A threshold is set above which the projection is masked. In this case, roughly thirty five percent (35%) of the maximum projection value is used. The resulting threshold projection data is shown in FIG. 4. This allows center-of-mass calculations to focus on the motion of the chest wall and the inner portion 408 has been masked out. The projection data with the liver motion removed is represented as a sinogram 412.

In the previous section, a system level overview of the operation of an embodiment was described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 500-600 are performed by a program executing on, or performed by firmware or hardware that is a part of, a computer, such as computer or master controller 120 in FIG. 1

Figure 5:
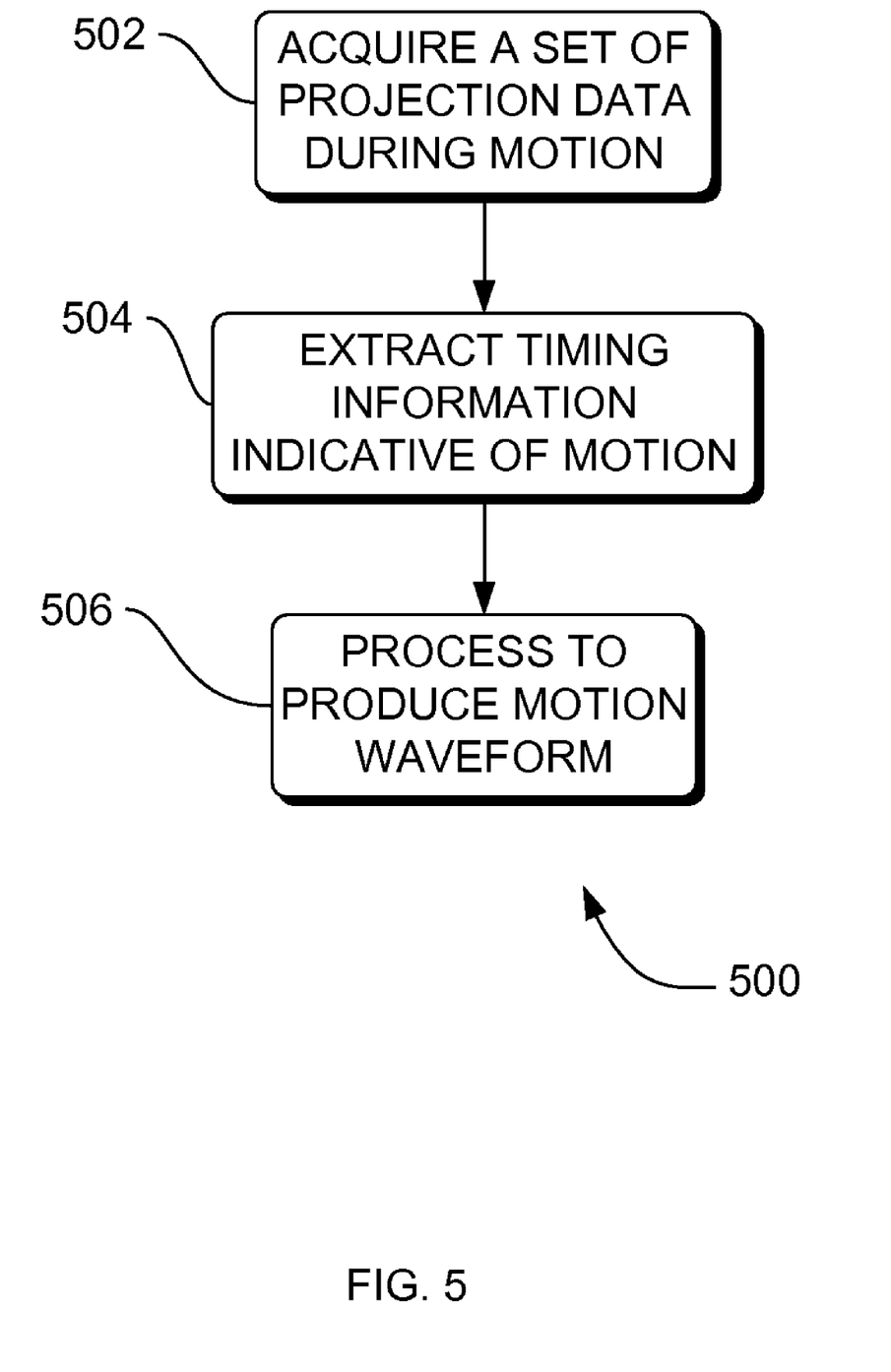
FIG. 5 is a flowchart of a method for extracting motion from projection data according to an embodiment.

FIG. 5 is a flowchart of a method 500 for extracting motion from projection data according to an embodiment. Method 500 solves the need in the art for extracting motion from projection data that is directly related to actual respiratory activity.

Method 500 begins with the acquisition of projection data in action 502. The acquire projection data 502 is generally selected such that sufficient information is provided to calculate locations of features causing X-ray attenuation. For example, consider CT projection data in which 1000 projections are acquired per gantry rotation. In this case, each of the 1000 projection angles can be tracked over time if multiple gantry rotations occur during the acquisition. Thus, in one single rotation of the gantry a single set of projection data (1000 projections) is acquired. Since the goal is to capture the respiratory cycle we need to acquire multiple sets of projection data. To acquire multiple sets of projection data we need an equal number of gantry rotations. In the case where the gantry mechanism rotates relatively quickly (less than or equal to 1 s per rotation) a seven rotation cycle is ample for capturing the respiratory cycle. To summarize, a single rotation produces 1000 projections, a seven cycle gantry rotation will produce 7000 projections (7 rotation×1000 projections/rotation). Once the set of projection data has been acquired in action 502 control passes to action 504 for further processing.

In action 504, timing information indicative of motion is extracted from the projection data. The extraction of timing information flows from the center of mass (CM) of the projections from different angles. The unit of the CM output is a detector column index. For example, prepped scan data has about 900 detector channels, so the CM for each projection would generally be in the range of 400-500. See items 402 and 406 in FIG. 4. It should be noted that this is only a one-dimensional CM value, not a set of coordinates. This is the CM calculation in the orthogonal direction to the projection angle. One can refer to this CM calculation as a function of time as ξ(t). The one-dimensional discrete CM formula used is:

$$\xi(t) = \frac{\sum_x x \cdot p(x, t)}{\sum_x p(x, t)},$$

Where t is the time into the current acquisition. Note that typically projection space is referred to as p(x,φ), but in our case with multiple gantry rotations and object motion we will use p(x,t). The projection angle φ also varies periodically with t. The resulting CM function ξ(t) is shown at item 702 of FIG. 7. Note that ξ(t) spans all projection angles, and the calculation of ξ(t) is dominated by the periodic gantry rotation as demonstrated in 702 of FIG. 7. Once the timing information has been extracted control passes to action 506 for further processing.

In action 506, the timing information is processed to produce a motion waveform that represents the respiratory cycle. In order to extract a CM waveform for each fixed conjugate projection angle pair, ξ(t) is sampled accordingly for each desired projection angle pair. Due to the conjugate nature of sampling, two sample points are available per gantry rotation for the signal produced from each projection angle pair. This provides the CM as a function of time for the axis perpendicular to the projection angle φ, which we will refer to as ξ(t). Qualitatively, it can be understood that a basic respiratory waveform can be seen from this plot when φ represents a horizontal projection angle. This sampling will produce a large number of $\xi_\phi(t)$ waveforms over a large range of projection angles. These many waveforms can be processed and combined using many methods. If projection angles are collected at uniform increments, then they may simply be resample to the CM sampling points and summed together. This will produce a very reliable output respiratory waveform.

Figure 6:
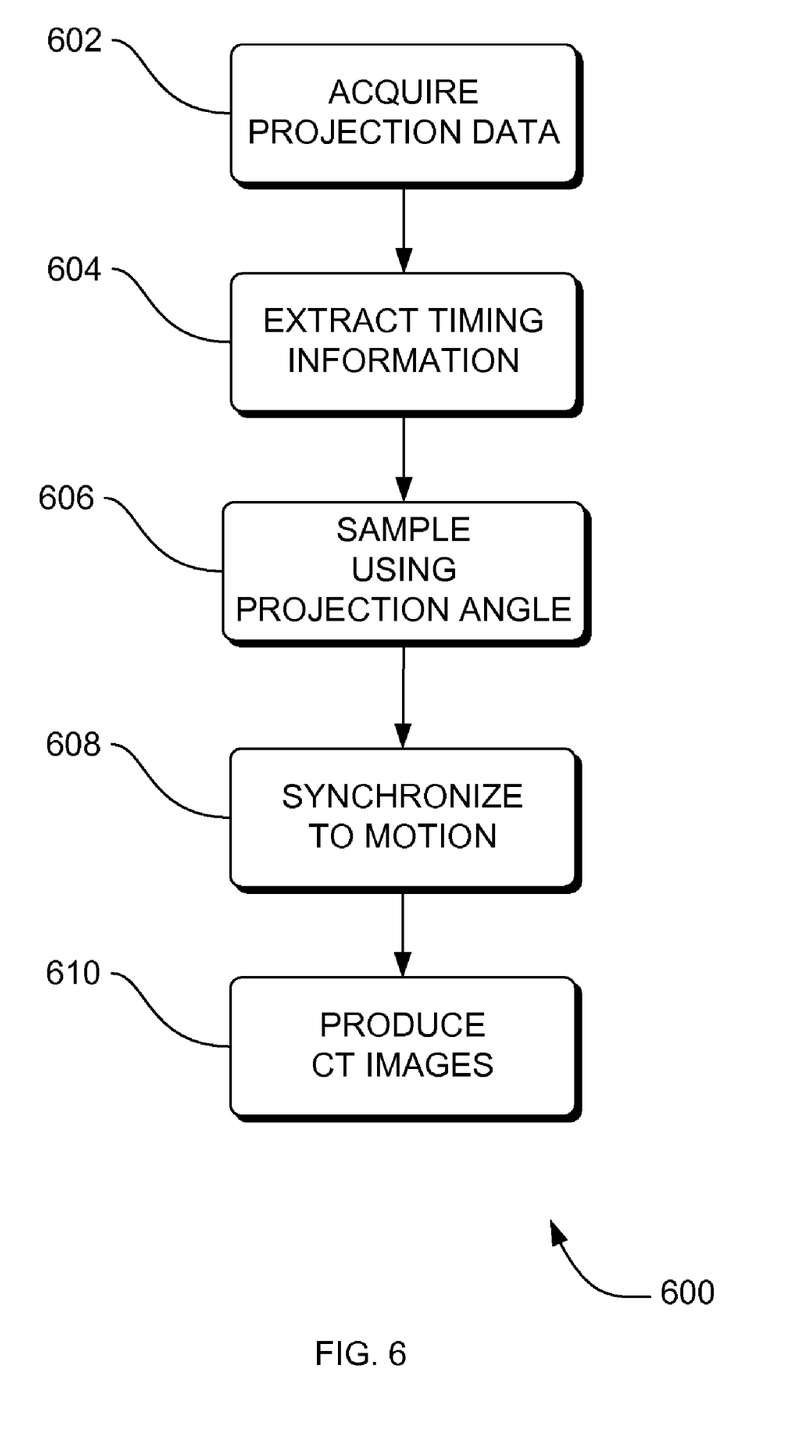
FIG. 6 is a flowchart of a method for extracting motion from projection data and for synchronizing captured images to the extracted motion according to an embodiment.

FIG. 6 is a flowchart of a method 600 for extracting motion from projection data according to an embodiment and applying the extracted motion to synchronize CT images. Method 600 solves the need in the art for extracting motion from projection data that is directly related to actual respiratory activity.

Method 600 begins with the acquisition of projection data. The projection data as shown above with action 502 are acquired by rotating the gantry 114 in the CT system 100. The acquired projection data set 602 contains the projection information that characterizes respiratory period at one point in time. By continuously rotating the detector 104 the periodicity information (rotation of the gantry) may be used to extract the periodicity of the center of mass (CM) at the region of interest, as depicted at action 504 of FIG. 5. Once the projection data has been acquired in action 602 control passes to action 604 for further processing.

In action 604, timing information is extracted from the acquired projection data. Since the timing information is a time-varying signal, various characteristics of the signal (magnitude, phase, rate of change) are useful for synchronizing the associated imaging data. As noted earlier the time-varying signal may be a signal representative of the respiratory flows into and out of the slice of tissue being monitored by the CT detector system. This timing information can be determined by sampling the projection data 602 at one or more projection angle. The method takes advantage of multiple projections from the same or conjugate projection angles (rotating gantry) to track motion. After the timing information has been extracted control passes to action to 606 for further processing.

In action, 606 the timing information is sampled at different projection angles. Edge detection, center-of-mass analysis, projection sum tracking, correlation-based approaches, and an array of other approaches may be implemented. The concept remains, however, that projection differences are tracked over time for a fixed projection angle and optionally its conjugate projection angle pair, meaning the projection angle differing by 180 degrees. In CT, this approach would analyze a fixed projection angle over time that is acquired once per gantry rotation, and twice if the conjugate projection is used. As a clear extension, a separate signal could be extracted for many projection angles over time, and then these can be processed together to derive a motion signal. The sampling of the projection data at around 270 degrees, and around 90 degrees, and conjugate sampling at 270 and 90 degrees should provide an adequate amount of continuous data points to reflect an accurate waveform of the respiratory cycle. Once the sample respiratory cycle has been determined control passes to action 608 for further processing.

In action 608, the CT images are synchronized to the respiratory cycle. After the timing information has been processed to provide the desired temporal correspondence with the motion of the respiratory phase, the imaging data is synchronized with the motion. In addition, the extracted motion can be used in respiratory gating in order to decrease the irradiation of healthy tissue. That is, the margins that are added in order to ensure that the tumor is within the applied field can be reduced by using respiratory gating, and thereby the proportion of irradiated healthy tissue can be decreased.

As described above, the processing may yield a time value such as the start of a motion, or of another phase or temporal event during the motion or it may yield a trigger signal of some kind. Synchronizing of the imaging data can be done prospectively by using a trigger signal output to initiate acquisition of imaging data or retrospectively by comparing the time value of the start of a motion to time stamps associated with the imaging data or internal gating. See P. Salla, G. Avinash, S. Sirohey, and T. Pan. "Systems and methods for retrospective internal gating." US Patent Application 2004/0258286 A1. The disclosure in US Patent Application 2004/0258286 A1 is hereby incorporated by reference in its entirety. After synchronizing the CT images to the respiratory cycle control passes to action 610 for further processing.

In action 610, the CT images are displayed or produced in a suitable medium. In particular, the user can use the user interface 122 firstly to display reconstructed images output from the means for image reconstruction 118, and secondly to define parameters useful for the master controller 120 to extract regions of interest from the reconstructed images in order to generate images that can be used by the user. The user interface 122 includes a window and virtual buttons. The user can use the window to display reconstructed images and destination images in which the results of operations carried out by the user on the reconstructed images are stored. Each reconstructed image is associated with a corresponding destination image.

In some embodiments, methods 500-600 are implemented as a computer data signal embodied in a carrier wave, that represents a sequence of instructions which, when executed by a processor, such as processor 204 in FIG. 2, cause the processor to perform the respective method. In other embodiments, methods 500-600 are implemented as a computer-accessible medium having executable instructions capable of directing a processor, such as processor 204 in FIG. 2, to perform the respective method. In varying embodiments, the medium is a magnetic medium, an electronic medium, or an optical medium.

Figure 7:
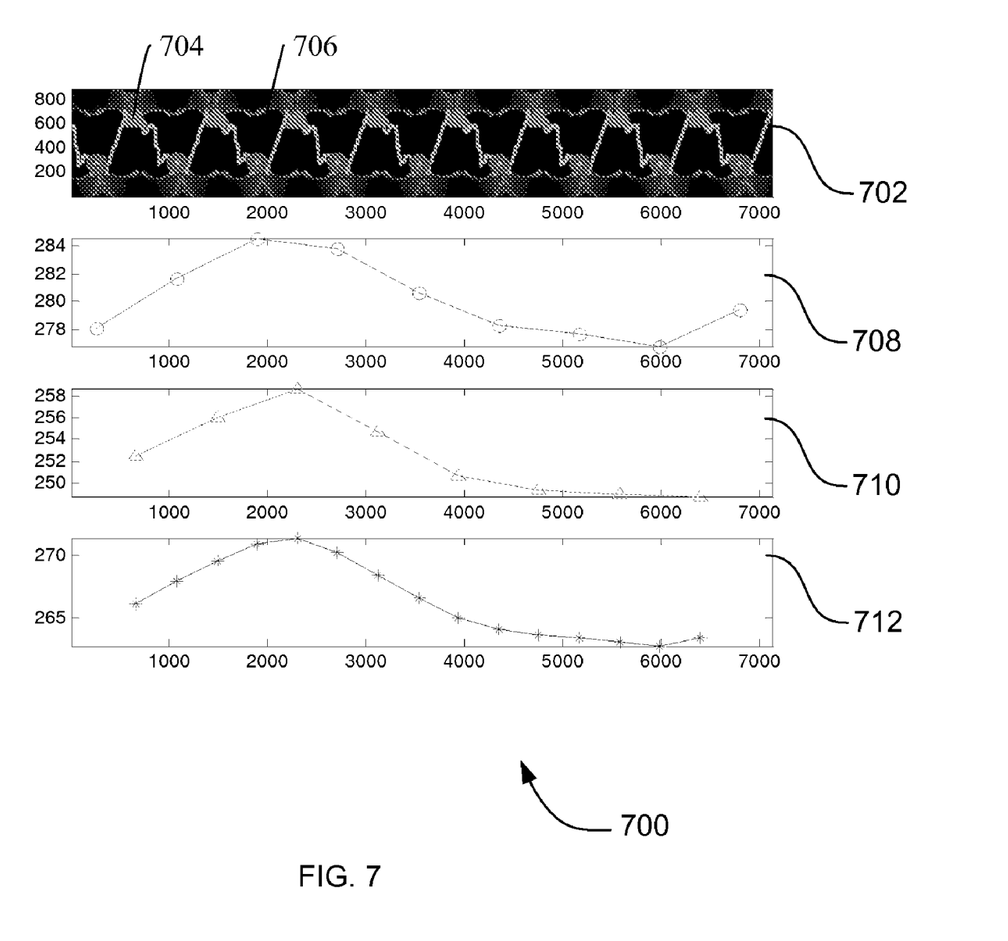
FIG. 7 is a diagram of the projection data, the projection data sampled at a first projection angle, the projection data sampled at a second projection angle and conjugate sampling of the projection data in accordance to an embodiment.

Referring to FIG. 7, a particular implementation 700 is described in conjunction with the system overview in FIGS. 1 and 2 and the methods described in conjunction with FIGS. 6 and 7. Curves 702, 708, and 710 demonstrate the process of obtaining a single $X_{f,filt}(t)$ waveform 712. The x-axis is projection number, and the y-axis is detector channel. The projection data and the x(t) curve is plotted in curve 702. Label 706 represents the samples of x(t) each time the gantry passes the 270 degree projection angle. Label 704 represents samples at the 90 degree projection angle. Curve 708 is a plot of the samples of the x(t) function for the 270 degree projection angles. Curve 710 is a plot of 888 minus the samples of the x(t) function for the 90 degree projection angles. The number 888 is chosen because it is the number of detector channels. Curve 712 is the result of combining the signals from curve 708 and 710 in a conjugate sampling fashion and filtering to remove the offset. This is the waveform $X_{f,filt}(t)$ for f at 90 degrees.

Apparatus 120 components of the CT detector system 100, and the image reconstruction 118 can be embodied as computer hardware circuitry (FIG. 2) or as a computer-readable program, or a combination of both. In another embodiment, system 100 is implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer or master controller 120 in FIG. 1, or on at least as many computers as there are components.

CONCLUSION

A method and apparatus for extracting motion from projection data is described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, the embodiment was described in the context of the cine acquisition method. In general, similar techniques may be applied to helical scanning methods by applying a low-pass filter at the end to remove bias effects from patient translation. The methodology relies on tracking center of mass (CM), or more specifically, changes in the scan data due to changes in chest and abdominal anatomy throughout the respiratory cycle. Alternatively, one could consider using an external marker on the patient's chest that could be tracked in the CT raw projection data to serve as a surrogate marker for respiratory phase. Additionally, while described in procedural terms, one of ordinary skill in the art will appreciate that implementations can be made in an object-oriented design environment or any other design environment that provides the required relationships. In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

We claim:

1. A method to extract motion from projection data acquired by a CT detector system, the method comprising:
   acquiring a set of projection data during motion;
   extracting timing information from at least a portion of the projection data, the timing information being indicative of the motion; and
   processing the timing information projection data from at least a portion of the projection data to produce a motion waveform,
   wherein the processing further comprises masking an inner portion of each projection to focus a center-of-mass analysis on an outside portion of a region of interest where a respiratory signal in the set of projection data is most evident,
   wherein the projection data includes measured projection data and interpolated projection data generated by a helical interpolation technique.

2. The method as recited in claim 1, wherein the set of projection data includes multiple projections from a rotating gantry.

3. The method as recited in claim 2, wherein processing the timing information includes sampling the set of projection data at a first projection angle.

4. The method as recited in claim 3, wherein processing the timing information includes sampling the set of projection data at a second projection angle.

5. The method as recited in claim 2, wherein processing the timing information includes conjugate sampling the set of projection data.

6. The method as recited in claim 2, the method further comprising:
   using the motion waveform to synchronize CT images produced by the CT detector system with the motion.

7. The method as recited in claim 1, wherein processing the timing information comprises processing to extract a peak, phase, or rate for a time-varying signal that corresponds with the motion.

8. The method as recited in claim 2, wherein processing the timing information includes a mask operator for masking a portion of the projection data.

9. An apparatus for extracting motion from projection data acquired by a CT detector system, the apparatus comprising:
   a processor;
   a non-transitory computer-accessible medium operably coupled to the processor and having executable instructions that are executed by the processor and that are operable to:
      acquire a set of projection data during motion;
      extract timing information from at least a portion of the projection data, the timing information being indicative of the motion; and
      process the timing information projection data from at least a portion of the projection data to produce a motion waveform;
   wherein the process further comprises generating a mask of an inner portion of each projection to focus a center-of-mass analysis on an outside portion of a region of interest where a respiratory signal in the set of projection data is most evident,
   wherein the projection data includes multiple projections from a rotating gantry,
   wherein the projection data includes measured projection data and interpolated projection data generated by a helical interpolation technique.

10. The apparatus as recited in claim 9, wherein processing the timing information includes sampling the set of projection data at a first projection angle.

11. The apparatus as recited in claim 10, wherein processing the timing information includes sampling the set of projection data at a second projection angle.

12. The apparatus as recited in claim 9, wherein processing the timing information includes conjugate sampling the set of projection data.

13. The apparatus as recited in claim 9, wherein processing includes using the motion waveform to synchronize CT images produced by the CT detector system with the motion.

14. The apparatus as recited in claim 9, wherein processing the timing information comprises processing to extract a peak, phase, or rate for a time-varying signal that corresponds with the motion.

15. The apparatus as recited in claim 9, wherein processing the timing information includes a mask operator for masking a portion of the projection data.

16. A non-transitory computer-accessible medium having executable instructions for extracting motion from projection data from a rotating gantry in a CT detector system, the executable instructions capable of directing a processor to perform:

acquiring a set of projection data during motion, wherein the projection data includes measured projection data and interpolated projection data generated by a helical interpolation technique;

extracting timing information from at least a portion of the projection data, the timing information being indicative of the motion; and     processing the timing information projection data from at least a portion of the projection data to produce a motion waveform,     wherein the processing further comprises masking an inner portion of each projection to focus a center-of-mass analysis on an outside portion of a region of interest where a respiratory signal in the set of projection data is most evident.

17. The computer-accessible medium of claim 16, wherein the executable instructions capable of directing the processor to perform the extracting motion further comprise executable instructions capable of directing the processor to perform one or more:

sampling the set of projection data at a first projection angle;

sampling the set of projection data at a second projection angle; and     conjugate sampling the set of projection data.

18. The computer-accessible medium of claim 16, wherein the executable instructions capable of directing the processor to perform the extracting motion further comprise executable instructions capable of directing the processor to perform:

processing to extract a peak, phase, or rate for a time-varying signal that corresponds with the motion.

19. The computer-accessible medium of claim 16, wherein the executable instructions capable of directing the processor to perform the extracting motion further comprise executable instructions capable of directing the processor to perform:

masking a portion of the projection data.

20. The computer-accessible medium of claim 16, wherein the executable instructions capable of directing the processor to perform the extracting motion further comprise executable instructions capable of directing the processor to perform:

sampling the set of projection data at one or more projection angle; and     using the motion waveform to synchronize CT images produced by the CT detector system with the motion.

\* \* \* \* \*